United States Patent [19]

Willard, Sr.

[11] 4,067,713

[45] * Jan. 10, 1978

[54] METHOD OF IMPROVING THE FERTILITY OF SOIL AND THE SOIL THUS PREPARED

[75] Inventor: John Wesley Willard, Sr., Rapid City, S. Dak.

[73] Assignee: CAW Industries, Inc., Rapid City, S. Dak.

[*] Notice: The portion of the term of this patent subsequent to July 8, 1992, has been disclaimed.

[21] Appl. No.: 749,285

[22] Filed: Dec. 10, 1976

Related U.S. Application Data

[63] Continuation-in-part of Ser. No. 593,712, July 7, 1975, which is a continuation-in-part of Ser. No. 317,097, Dec. 20, 1972, Pat. No. 3,893,943, which is a continuation-in-part of Ser. No. 108,198, Jan. 20, 1971, abandoned.

[51] Int. Cl.$^2$ ............................................. C05F 11/02
[52] U.S. Cl. ............................................. 71/24; 71/63; 71/64 C; 71/64 SC
[58] Field of Search ....................... 44/1 R, 1 B, 6, 27; 252/446; 71/1, 24, 27, 63, 64 C, 64 SC; 47/1 R, 48.5, 58, DIG. 10

[56] References Cited

U.S. PATENT DOCUMENTS

| | | | |
|---|---|---|---|
| 3,272,753 | 9/1966 | Wixon | 252/532 X |
| 3,350,319 | 10/1967 | Schonfeldt | 252/532 X |
| 3,351,558 | 11/1967 | Zimmerer | 252/532 X |
| 3,377,293 | 4/1968 | Shephard | 252/313 S |
| 3,453,144 | 7/1969 | Morgan et al. | 252/532 X |
| 3,657,151 | 4/1972 | Noble | 252/453 X |
| 3,893,943 | 7/1975 | Willard, Sr. | 252/451 X |

*Primary Examiner*—Charles N. Hart
*Assistant Examiner*—Ferris H. Lander
*Attorney, Agent, or Firm*—L. S. Van Landingham, Jr.

[57] ABSTRACT

Soil is intimately contacted with water containing a catalytically effective amount of a novel catalyst to improve the fertility thereof. In a preferred variant, the water which is intimately contacted with the soil may also contain catalyst treated lignite. Plants grown in the treated soil are more vigorous and resistant to disease or adverse environmental conditions. The yields are higher in instances where the plants are grown commercially for food or fiber, and the plants have a more pleasing appearance in instances where they are grown for decorative purposes. The catalyst is prepared by a process including the steps of admixing a water soluble alkali metal silicate with an aqueous medium containing carefully controlled amounts of water soluble substances which are sources of calcium ion and magnesium ion, reacting the same to produce an aqueous colloidal suspension of the reaction product, admixing a micelle forming surfactant with the aqueous medium, and agitating the aqueous medium containing the colloidal particles and surfactant to form catalyst containing micelles. The catalyst treated lignite is prepared by a process including intimately contacting lignite with an aqueous medium containing the novel catalyst until it is soluble. Presently preferred processes for preparing the novel catalyst and the water soluble catalyst treated lignite are described.

24 Claims, No Drawings

METHOD OF IMPROVING THE FERTILITY OF SOIL AND THE SOIL THUS PREPARED

RELATED APPLICATIONS

This application is a continuation-in-part of copending application Ser. No. 593,712, filed July 7, 1975 on behalf of John W. Willard, Sr. for A PROCESS FOR TREATING SOLID CARBONACEOUS FOSSIL FUELS AND THE PRODUCTS THUS PREPARED. Application Ser. No. 593,712 was a continuation-in-part of application Ser. No. 317,097, now U.S. Pat. No. 3,893,943, filed Dec. 20, 1972, for NOVEL CATALYST AND PROCESS FOR PREPARING THE SAME. Application Ser. No. 317,097, was a continuation of application Ser. No. 108,198, now abandoned, filed Jan. 20, 1971, for NOVEL CATALYST AND PROCESS FOR PREPARING THE SAME.

THE BACKGROUND OF THE INVENTION

1. The Field of the Invention

This invention broadly relates to a method of treating soil. In some of its more specific aspects, the invention is concerned with a method of improving the fertility of soil whereby plants grown in the treated soil are more vigorous and resistant to disease and adverse environmental conditions. The invention also relates to the treated soil characterized by improved fertility thus prepared.

2. The Prior Art

Plants grown in soil require moisture and a number of plant nutrients for vigorous growth such as water soluble compounds of nitrogen, phosphorous, potassium, calcium, magnesium, iron and other essential elements. The plant nutrients must be in a chemical form which allows them to be utilized by the plants. Thus, the mere presence of essential elemental substances in the soil does not necessarily mean that the plants are able to utilize them effectively. Also, the plant nutrients should be present in the proper concentration and ratios for the most effective utilization by the plants. As is well known, many soils are deficient in one or more plant nutrients and/or the plant nutrients which are present are not in a chemical form easily utilized by the plants.

A number of attempts have been made heretofore to overcome the above mentioned limitations and disadvantages of soils. The most common approach at the present time usually involves analyzing the soil to determine the available plant nutrients, and then adding plant nutrients in which the soil is deficient in the form of chemical fertilizers. This method is expensive initially and, as a general rule, it must be repeated each year to achieve the best results as all or part of the added plant nutrients are consumed by the growing plants. The use of conventional chemical fertilizers does not have any appreciable beneficial effect on plant nutrients present in the soil in an unavailable form. Additionally, chemical fertilizers do not increase the resistance of the growing plants to disease or adverse environmental conditions.

It will be apparent from the foregoing that the art has long sought an entirely satisfactory method of treating soil which not only assures that the necessary plant nutrients are present, but also aids in converting normally unavailable plant nutrients in the soil to a form which growing plants are capable of utilizing. Additionally, the treated soil also should provide the growing plants with an environment which results in greater resistance to disease and/or adverse environmental conditions. However, a suitable method of treating soil to provide these beneficial effects simultaneously was not available prior to the present invention.

THE SUMMARY OF THE INVENTION

The present invention provides a novel method of proving the fertility of soil, and further provides the resultant soil characterized by improved fertility. This is accomplished both inexpensively and conveniently by intimately contacting the soil with water containing a catalytically effective amount of a novel catalyst. Preferably, the water which is intimately contacted with the soil also contains water soluble catalyst treated lignite. Plants grown in the treated soil are more vigorous and resistant to disease or adverse environmental conditions. Yields are higher in instances where the plants are grown commercially for food or fiber, and the plants have a more pleasing appearance in instances where they are grown for decorative purposes. Reference may be had to the following detailed description and the specific examples for preferred variants and embodiments of the invention, and for presently preferred processes for preparing the aforementioned novel catalyst and water soluble catalyst treated lignite.

THE DETAILED DESCRIPTION OF THE INVENTION INCLUDING CERTAIN PRESENTLY PREFERRED VARIANTS AND EMBODIMENTS THEREOF

In practicing the present invention, soil to be treated is intimately contacted with water containing a catalytically effective amount of the novel catalyst described hereinafter. The water also may contain lignite which has been pretreated with the catalyst until it is soluble to thereby further improve the results. It will be appreciated that there are certain preferred variants and embodiments of the invention which produce exceptionally good results, and that such preferred variants and embodiments will be discussed in greater detail hereinafter and/or illustrated in the specific examples.

The water that is intimately contacted with the soil need contain only a catalytically effective amount of the catalyst, but much larger amounts may be present as the catalyst appears to be harmless when present in reasonable amounts. For example, the water usually contains about 0.000001–1000 parts per million (ppm) of the catalyst, and about 0.00001–200 ppm often produces very good results. In some instances, the water contains about 0.00005–100 ppm of the catalyst, and in other instances, about 0.005–50 ppm of the catalyst. Very small amounts of the catalyst may be present in the water in still other instances, such as about 0.000001–5 ppm or about 0.01–1 ppm. For even better results, the water also contains water soluble catalyst treated lignite in an amount of, for example, about 0.000001–1000 ppm, or about 0.00001–200 ppm. In other instances, the water may contain about 0.00005–100 ppm, or about 0.005–50 ppm, of the catalyst treated lignite. In still other instances, the water need contain only about 0.000001–5 ppm, and often only about 0.01–1 ppm of the catalyst treated lignite. As is apparent from the above, the catalyst treated lignite also need be present in only substantially catalytic amounts, but much large amounts may be present as it likewise appears to be harmless in reasonable amounts.

The catalyst and catalyst treated lignite are prepared as described hereinafter, and the quantities of the catalyst and the catalyst treated lignite are calculated by weight and on a dry solids basis. The catalyst treated lignite often contains the catalyst which was used in its preparation and, in such instances, the weight of catalyst solids initially present is included in the calculations to determine the total amount of catalyst solids. When the catalyst treated lignite is present, the weight ratio of catalyst solids to catalyst treated lignite solids may vary over wide ranges such as, for example, from about 1:200 to 200:1 in most instances, and from 1:50 to 50:1 in some instances. Usually, the weight ratio of catalyst solids to catalyst treated lignite solids is about 1:10 to 1:30, and often is about 1:20.

The water containing the catalyst and/or catalyst treated lignite may be intimately contacted with the soil in any convenient manner. For example, the soil may be sprayed, sprinkled, flooded or irrigated therewith, and this may be done before, during or after tilling or agitating the soil. In one variant, the water containing the catalyst and/or catalyst treated lignite may be applied to openings made in the soil such as furrows, holes, depressions and the like to receive, for example, seeds or plants for transplanting. The water containing the catalyst and/or catalyst treated lignite may be applied to soil in situ on a large scale such as when treating flower beds, garden plots, or open fields. It is also possible to treat relatively small quantities of soil and in such instances, it is usually preferred that topsoil be removed and intimately contacted with the water in a vat or other large container, with or without a mechanical mixing device or other agitating means.

Regardless of the specific method that is used, it is only necessary to intimately contact the soil with water containing the catalyst and/or catalyst treated lignite in a quantity sufficient to deposit a catalytically effective amount thereof in the soil. For example, when treating soil in situ, the water containing the catalyst and/or catalyst treated lignite may be applied at a rate to provide the equivalent of a layer about 0.0001–10 inches in depth over the soil surface. Usually a depth of about 0.001–1 inch produces good results and, in some instances, a depth of about 0.1–0.5 inch is very satisfactory. Where the water containing the catalyst and/or catalyst treated lignite is applied by spraying, sprinkling or the like, and especially when the soil is treated with agitation, the application may be at a rate sufficient to only slightly moisten the soil. In other instances, the rate of application is sufficient to saturate the soil, and in still other instances, the rate of application may vary between slightly moistening and saturating the soil. Often the rate of application may vary between about 0.000001% by weight up to saturation of the soil, or from about 0.001% by weight up to saturation of the soil, based upon the weights of the soil and the water containing the catalyst and/or catalyst treated lignite. In other instances, the water containing the catalyst and/or catalyst treated lignite may be applied to the soil on a weight basis at the rate of, for example, about 0.01–50% by weight, or at the rate of about 1–10% by weight. When a potting soil characterized by increased fertility is prepared, then the treated soil may be partially or completely air dried or dried by other means such as by application of heat. Additionally, it is preferred that the catalyst and/or catalyst treated lignite be admixed uniformly throughout the potting soil.

The water containing the catalyst and/or catalyst treated lignite may also contain one or more plant nutrients or micronutrients when desired. The most common plant nutrients added to soil include compounds containing potassium, nitrogen and/or phosphorous in forms which are readily utilized by plants. Micronutrients and other nutrients also may be added when desired, and especially when the soil is deficient therein. Commercially available sources of plant nutrients and micronutrients may be used when practicing the present invention. Surprisingly, the amounts of plant nutrients and micronutrients required to achieve a given degree of effectiveness is much lower when practicing the present invention than in the absence of the catalyst and/or catalyst treated lignite. Often less than 2/3 and usually less than one half of the amounts of plant nutrients or micronutrients recommended by the prior art need be applied.

In many instances, the application is at the rate of about 5–75% by weight or about 25–50% by weight of that normally applied to achieve a given degree of effectiveness in the absence of the catalyst and/or catalyst treated lignite.

Surprisingly, the soil has a higher concentration of plant nutrients and micronutrients available to plants for growth following treatment with the water containing the catalyst and/or catalyst treated lignite. Thus, the treated soil is altered or modified in some manner which is not fully understood at the present time so as to allow plants to utilize nutrients and micronutrients which were previously unavailable for utilization. It is therefore apparent that the fertility of the soil may be increased by two separate and distinct routes, i.e., by increasing the degree of effectiveness of the available plant nutrients and micronutrients at given concentrations, and/or by modifying or altering the normally unavailable plant nutrients or micronutrients to forms which may be easily assimilated by plants. This unusual and unexpected combination of beneficial results has not been achieved heretofore by merely adding chemical fertilizers of the prior art types.

The treated soil has still other unusual and unexpected advantages. Plants grown in the treated soil are more vigorous and resistant to disease and adverse environmental conditions. The roots of the plants are longer, stronger and appear in greater numbers, and are more capable of supplying the plants with water and nutrients. Plants commence to grow earlier and continue to grow more vigorously. The plants also are more resistant to disease, and are not as adversely affected by insufficient moisture, excessive moisture, insufficient sun, too much sun and other environmental conditions. Yields are higher with respect to plants producing a commercially valuable commodity such as food and/or fiber, and shrubbery, flowers and plants in general grown for decorative purposes are more beautiful.

As a general rule, prior art practices may be followed in growing plants in the treated soil. Suitable prior art practices useful in growing a specific plant species are well known. Also, the plant nutrients and micronutrients, including the amounts thereof, required for growing a specific plant species are well known and may be selected in accordance with the prior art teachings when viewed in the light of the present invention. There are numerous publications in this field which disclose the foregoing. For example, the United States Department of Agriculture publishes and distributes to the public a large number of publications concerned with the propagation of all types of plants, including the plant nutrients and micronutrients needed therefor. The disclosures of those publications are incorporated herein in by reference. The procedures recommended therein may be followed in practicing the present invention with the exception of using the treated soil disclosed herein rather than untreated soil.

The term "soil" as used in the specification and claims is intended to embrace suitable growth media in general for plants. For instance, the term "soil" is intended to include soil per se, and other suitable growth media such as peat, peat moss, vermiculite, pearlite, sand, compost, admixtures of two or more of the foregoing, and the like.

The preparation of the novel catalyst or synergist of the invention is described immediately hereinafter, and the preparation of the catalyst treated lignite is described thereafter. In instances where an aqueous suspension or solution of the catalyst and/or the catalyst treated lignite is used in practicing the method of the invention, then the concentration of the catalyst and/or the catalyst treated lignite often may be as set out hereinafter.

PREPARATION OF THE CATALYST

The catalyst used in practicing the present invention may be prepared as described below. In the presently preferred process for preparing an aqueous suspension of the catalyst, a water soluble alkali metal silicate is admixed and reacted with an aqueous solution of a water soluble dissolved substance which is a source of calcium ion and a water soluble dissolved substance which is a source of magnesium ion to produce a finely divided or colloidal suspension of the reaction product. The aqueous solution contains the dissolved substances initially in amounts to provide between about $1 \times 10^{-4}$ and $1 \times 10^{-1}$ mole per liter each of calcium ion and magnesium ion, preferably between about $1 \times 10^{-3}$ and $1 \times 10^{-2}$ mole per liter, and for still better results between $1 \times 10^{-3}$ and $6 \times 10^{-3}$ mole per liter. The dissolved substances should also be present in amounts to provide a molar ratio of calcium ion to magnesium ion between about 2.0:1.0 and 1.0:2.0, and preferably about 1.5:1.0 and 1.0:1.5. For best results, the aqueous medium should contain the dissolved substances in amounts to provide between about $2.5 \times 10^{-3}$ and $3.0 \times 10^{-3}$ mole per liter each of calcium ion and magnesium ion, and the molar ratio of calcium ion to magnesium ion should be about 1.0:1.0, e. g., $2.9 \times 10^{-3}$ mole per liter of calcium ion and $2.7 \times 10^{-3}$ mole per liter of magnesium ion. The alkali metal silicate should have an alkali metal oxide to silicon dioxide ratio between about 0.9:1.0 and less than 2.0:1.0, and preferably between about 0.9:1.0 and 1.2:1.0. The alkali metal silicate should be admixed with the aqueous medium in an amount of about 0.05-2 moles per liter, preferably about 0.1-1 mole per liter, and for still better results about 0.2-0.5 mole per liter. For best results, the alkali metal silicate should be an alkali metal meta-silicate having an alkali metal oxide to silicon dioxide ratio of about 1:1, and it should be admixed with the aqueous medium in an amount to provide about 0.2-0.3 mole per liter, e.g., about 0.25 mole per liter.

Examples of sources of calcium ion and magnesium ion for use in preparing the aqueous solution include mineral acid salts such as the halides, sulfates, bisulfates, nitrites, and nitrates of calcium and magnesium. The chlorides are usually the preferred halides, and both calcium and magnesium chloride are soluble and may be used. Magnesium sulfate and bisulfate are soluble and often are the preferred sources of magnesium ion. Calcium sulfate is only slightly soluble in water and usually is not a preferred source of calcium ion, but calcium bisulfate is somewhat more soluble. While calcium and magnesium nitrite or nitrate are soluble in water and may be used, these substances are not preferred in most instances. The sources of calcium ion and magnesium ion are dissolved in the aqueous medium in amounts to provide calcium ion and magnesium ion within the above ranges. Complete ionization is assumed when calculating the quantities to be dissolved and any desired order of addition is satisfactory. For example, the source of calcium ion may be added to the aqueous medium before, during or after the source of magnesium ion.

The alkali metal silicate to be admixed with the aqueous medium is preferably a water soluble sodium or potassium silicate having an alkali metal oxide ($M_2O$) to silicon dioxide ($SiO_2$) mole ratio between about 0.9:1.0 and less than 2.0:1.0, and preferably between about 0.9:1.0 and 1.2:1.0. The best results are usually obtained with an alkali metal metasilicate having an alkali metal oxide to silicon dioxide ratio of about 1:1. Hydrated alkali metal silicates dissolve faster and should be used for best results when the alkali metal silicate is added in solid form. In instances where an anhydrous alkali metal silicate is used, it may be desirable to dissolve it in water and then add the solution to the aqueous medium. Sodium metasilicate is preferred and usually a hydrated sodium metasilicate such as the pentahydrate gives the best results.

Carbonate ion and/or bicarbonate ion should not be present in the aqueous medium in substantial concentrations as the calcium ion and magnesium ion are precipitated in the form of their respective carbonates. The free carbonate ion and/or bicarbonate ion concentrations in the aqueous medium should not exceed about 10 parts per million by weight based upon the combined weight of the water and the ingredients added thereto and for this reason, the alkali metal silicates should be substantially free of carbonate ion and bicarbonate ion. A small amount of precipitated calcium carbonate and/or magnesium carbonate may be present in the aqueous medium provided additional calcium ion and magnesium ion are available to meet the above defined concentrations.

Distilled water and/or deionized water are usually preferred over a natural or untreated water when preparing the aqueous medium. In instances where water is used which contains substantial initial concentrations of alkaline earth metal ions, then this should be taken into consideration in calculating the amounts of the sources of calcium ion and magnesium ion which are necessary to arrive at the final concentrations previously discussed.

An electrolyte which aids in the preparation of colloidal suspensions may be present in the aqueous medium at the time of admixing the alkali metal silicate therewith. Examples of electrolytes include those used in preparing prior art colloidal suspensions such as the alkali metal halides, sulfates and bisulfates. Sodium chloride, sodium sulfate and sodium bisulfate are usually preferred. The electrolyte should be added in small amounts such as, for example, about 0.00001-0.1 mole per liter, but often larger or smaller amounts may be present.

The conditions under which the alkali metal silicate is admixed with the aqueous medium and reacted with the sources of calcium ion and magnesium ion are not critical provided the reaction mixture is maintained in the liquid phase. The reaction temperature may be, for example, between the freezing point and boiling point of water under the existing pressure conditions. At atmospheric pressure, the temperature is usually about 10°–90° C and often a more convenient temperature is about 20°–50° C. In many instances, ambient or normal room temperature is satisfactory.

The degree of agitation is not critical, and mild to vigorous agitation may be employed during addition of the alkali metal silicate. For the best results, the aqueous medium should be agitated sufficiently to assure rapid and uniform admixing of the alkali metal silicate. After completing the addition of the alkali metal silicate, when desired the agitation may be continued for a sufficient period of time to assure complete reaction and aging of the resulting colloidal suspension, such as for approximately 1–5 minutes to one hour or longer.

Upon admixing the alkali metal silicate with the aqueous medium, it takes on a turbid appearance but in most instances no significant amount of visible precipitate is formed. The colloidal suspension of the reaction product thus produced should be strongly basic and may have a pH value of, for example, approximately 10–14 and preferably about 11–13, and for best results about 12. In view of this, the initial pH value of the aqueous medium containing the dissolved sources of calcium ion and magnesium ion is of importance and should be about 6–9 and preferably about 7–8. When necessary, it is possible to adjust the pH value of the aqueous medium to the foreging levels either before during or after addition of the alkali metal silicate by adding bases such as sodium or potassium hydroxide, or mineral acids such as sulfuric or hydrochloric acid.

The colloidal suspension may be stored for several weeks or longer while awaiting the further treatment described hereinafter. In instances where the colloidal suspension is to be stored over a substantial period of time, the pH value should be maintained at the above described level and the storage vessel is preferably a tightly capped polyethylene bottle or other inert plastic container which prevents the contents from absorbing carbon dioxide from the atmosphere.

The colloidal suspension of the reaction product is not suitable for use as a catalyst as prepared and it should be agitated sufficiently in the presence of a micelle-forming surfactant to form catalyst-containing micelles. The degree of agitation, the length of the agitation period, and the amount of the micelle-forming surfactant that is present in the colloidal suspension are controlled at levels favorable to the formation of micelles. For example, the surfactant may be present in an amount of about 0.001–0.1 mole per liter and preferably about 0.03–0.07 mole per liter for most surfactants. Smaller or larger amounts may be effective with some surfactants such as 0.0001 mole per liter or less, or 0.2 mole per liter or more. About 0.05 mole per liter often gives the best results with many surfactants.

The minimum period of agitation and the minimum degree of agitation that are required for micelle formation varies somewhat with temperature and the type and amount of surfactant. As is well understood in this art, gradually increasing these variants in the presence of an effective amount of the micelle-forming surfactant will result in micelle formation when the proper levels are reached. As a general rule, longer periods of agitation and/or more vigorous agitation are required to form micelles at lower temperatures approaching the freezing point of the colloidal suspension than at higher temperatures approaching the boiling point. In instances where the aqueous suspension has a temperature of approximately 50°–90° C., then mild agitation over a period of about 10–60 minutes is satisfactory. Often longer or shorter periods of mild to vigorous agitation may be employed such as from about 1–5 minutes to several hours at temperatures varying, respectively, between the boiling point and the freezing point. When desired, the agitation may be continued long after the catalyst-containing micelles are formed as continued agitation does not seem to have an adverse affect.

As a general rule, the micelle-forming surfactants known in the prior art may be used in practicing the present invention. Micelle-forming surfactants used in the emulsion polymerization of monomeric organic compounds are disclosed in the text *Synthetic Rubber,* by G. S. Whitby, et al, John Wiley & Sons Incorporated, New York (1954), and surface active agents in general are disclosed on pages 418–424 of the text *Organic Chemistry,* Fieser and Fieser, 2nd Edition, Reinhold Publishing Corporation, New York, New York (1950), the disclosures of which are incorporated herein by reference. Examples of surfactants disclosed in the above texts include the alkali metal soaps of long chain fatty acids, and especially the sodium and potassium soaps of fatty acids containing about 14–25 carbon atoms and preferably about 16–18 carbon atoms, and the sodium and potassium soaps of the rosin acids, abietic acid and the derivatives thereof. Other micelle-forming surfactants include fats and oils such as corn oil, cotton seed oil, castor oil, soy been oil and safflower oil which have been fully or partially saponified with alkali metal bases to produce mixtures including saponified long chain fatty acids, the mono- or di-glycerides thereof, and glycerin.

Examples of synthetic micelle-forming surfactants include the sulfonates of long chain alcohols prepared by hydrogenation of naturally ocurring fats and oils of the above types and especially sulfonated long chain alcohols containing about 10–20 and preferably about 12–14 carbon atoms, the alkali metal salts of the monosulfonates of monoglycerides such as sodium glyceryl monolaurate sulfonate, the sulfonates of succinic acid esters such as dioctyl sodium sulfosuccinate and the alkylaryl alkali metal sulfonates. Specific examples of presently preferred micelle-forming surfactants include sodium and potassium sulforicinoleate, tetrahydronaphthalene sulfonate, octahydroanthracene sulfonic acid, butyl naphthalene sulfonic acid, sodium xylene sulfonate, alkyl benzene sulfonic acid and potassium benzene sulfonate.

Sulfated long chain hydroxycarboxylic acids containing about 14–25 carbon atoms and preferably about 16–18 carbon atoms, and sulfated fats and oils containing hydroxycarboxylic acids of this type produce exceptionally good micelle-forming surfactants. At least 25% of the hydroxyl groups and preferably at least 50% should be sulfated, and up to 95–100% may be sulfated. It is usually preferred that the sulfated oils and/or long chain hydroxycarboxylic acids be neutralized with an alkali metal base, and that the corresponding alkali metal salts be added to the colloidal suspension in the form of an aqueous solution. The aqueous solution may contain at least 25% of water and preferably at least 34–40% by weight. Much larger percentages of water may be present when desired such as 75–80% or more by weight.

A very active catalyst is produced when using sulfated castor oil as the micelle-forming surfactant (Turkey Red Oil). Sulfated castor oil which has been purified sufficiently to be of U.S.P. or medicinal grade produces an exceptionally active catalyst. For the best results, the castor oil is reacted with about an equal weight of concentrated sulfuric acid (.g., 20% by weight $H_2SO_4$) at a temperature of approximately 25°-30° C. The mixture may be reacted for about two hours with stirring and is then neutralized with sodium hydroxide solution. The reaction mixture separates into three layers, i.e., an upper layer which is a water solution, an intermediate or oily layer, and a white curdy precipitate. The intermediate oily layer is separated from the upper and lower layers, and may be added to the colloidal suspension as the micelle-forming surfactant in an amount, for example, of 0.001-0.1 mole per liter, and preferably about 0.005 mole per liter.

The activity of the catalyst may be increased very markedly by cooling the aqueous catalyst suspension to a temperature approaching the freezing point such as about 0°-10° C., and then warming over one or more cycles. For best results, the aqueous catalyst suspension should be frozen and thawed over one or more cycles. The reason for the increased catalytic activity is not fully understood at the present time but cooling and then warming the aqueous catalyst suspension seems to increase the concentration of the catalyst-containing micelles and/or increases the catalytic activity thereof.

The aqueous suspension of the catalyst contains a relatively small percentage by weight of the active catalyst as produced. When desired, it may be concentrated by evaporating a portion of the water to produce a concentrated liquid catalyst suspension which may be stored and used more conveniently. It is also possible to prepare a dry catalyst concentrate by evaporating substantially all of the water. The preferred method of producing the dry catalyst concentrate is by flash evaporation using a technique analogous to that employed in preparing powdered milk. The catalyst concentrates produced upon partial or complete evaporation of the water content of the intially prepared aqueous suspension may be reconstituted by addition of water with little or no loss of catalytic activity. Preferably, the water is added to the dry catalyst concentrate under sufficiently vigorous conditions of agitation to assure that the catalyst micelles are resuspended and uniformly distributed.

In a further variant of the process for preparing the catalyst, at least one dissolved substance providing at least one amphoteric metal-containing ion is present in the aqueous medium at the time of reacting the alkali metal silicate with the substances providing calcium ion and magnesium ion. The substance or substances providing the amphoteric metal-containing ion or ions may be present, for example, in an amount sufficient to provide about 0.0001-10% and preferably about 0.01-0.5% by weight when calculated as the amphoteric metal oxide and based upon the weight of the alkali metal silicate. Preferred amphoteric metals include aluminum and/or zinc, and the preferred sources thereof include alkali metal aluminate and zincate of which sodium and/or potassium aluminate and/or zincate usually give the best results. The alkali metal aluminate and/or zincate may be added directly to the aqueous medium, or as the mineral acid salts, oxides and/or hydroxides which then form the alkali metal aluminate and/or zincate under the highly alkaline conditions that exist.

The aqueous catalyst suspension may be used in the concentration as produced, or it may be diluted with approximately 2-100,000 or more parts by weight of water prior to use. It is only necessary that the aqueous medium contain a catalytic amount of the catalyst and much larger than catalytic amounts may be present. For better results, in some instances the catalyst suspension as produced may be diluted with about 200-10,000 parts by weight of water, and for still better results in other instances, with about 500-1,000 parts by weight of water. The aqueous medium may, for example, have 0.000001-1% by weight and often about 0.0001-3% by weight of the catalyst, but larger or smaller amounts may be present. In some instances, the aqueous medium contains about 0.001-0.1% or 0.004-0.08% by weight of the catalyst, and in other instances about 0.006-007% by weight. The weight or weight percent of the catalyst is calculated on a dry solids basis, i.e., the total weight of the catalyst ingredients in the aqueous catalyst suspension as produced after removal of the water. The dry catalyst solids or liquid catalyst concentrate may be admixed with water and/or a micelle forming surface active agent to provide a catalytically effective catalyst micelle concentration such as in the quantities previously discussed. The pH of the diluted aqueous catalyst suspension to be used may be adjusted to a desired value by addition of a mineral acid such as sulfuric acid or a strong base such as alkali metal hydroxide. This variant is of importance when the catalyst suspension should be approximately neutral as used for a given purpose. This variant is also of importance where the aqueous catalyst suspension, when used for a specific purpose, should be strongly acidic or basic for better results.

The Preparation of Solutions Of Catalyst Treated Lignite

The aqueous solutions of catalyst treated lignite for use in practicing the method of the invention may be prepared as described hereinafter.

The lignite is intimately contacted in particulate form with an aqueous medium containing a catalytically effective amount of the novel catalyst described above. The lignite has active sites which are capable of reacting with at least one component of the aqueous medium in the presence of the catalyst, and it is contacted with the aqueous medium under liquid phase conditions until substantially all or a desired proportion of the active sites react. Thereafter, the lignite may be further treated as more fully described below.

The lignite need not be pretreated prior to treating with the aqueous medium other than, when deisred, crushing or otherwise reducing it to a suitable particle size. The particle size is not critical and may vary over wide ranges as the aqueous medium has remarkable penetration properties and is capable of penetrating large lumps. The particle size may be, for example, from 1 inch to −300 mesh (Tyler Screen) and preferably is about −10 mesh to −200 mesh, and for many applications is from −50 mesh to −100 mesh. It is understood that particles as large as 2, 3 or 4 inches, and often mine run lignite, may be treated but longer periods of contact with the aqueous medium may be necessary to allow sufficient time for adequate penetration and reaction. Also, particle sizes smaller than −300 mesh may be treated but the expense of grinding the lignite to such a fine particle size usually outweighs any advantages that are gained. The volume ratio of aqueous medium to lignite may vary over wide ranges. It is usually preferred that the aqueous medium be present in sufficient volume to allow the particles to be easily agitated therein such as by means of a prior art stirring or agitating device. The concentration of the catalyst in the aqueous medium also may vary over wide ranges as it is only necessary that a catalytic amount be present. Suitable catalyst concentrations are discussed in the above section relating to the preparation of the catalyst. The pH value of the aqueous treating medium may vary from about 1 to 13.5. The initial pH value is preferably greater than 7, and is usually about 8–11. There is a tendency for the pH value to decrease as the reaction proceeds to about 5–6. If desired, the pH value of the aqueous medium may be adjusted as the reaction proceeds by addition of a base such as an alkali metal hydroxide to thereby partially or fully restore the initial pH value. Sodium, potassium or ammonium hydroxides are useful for this purpose and sodium hydroxide is usually preferred.

The temperature of treatment may likewise vary over wide ranges and may be, for example, between the freezing point and the boiling point of the aqueous medium under the existing pressure conditions. Usually atmospheric pressure is preferred, and in such instances, the aqueous medium may have a temperature of approximately 0° C. and is often about 20°–60° C. Surprisingly, lower temperatures of treatment such as 0°–10° C. appear to enhance the rate and degree of oxidation of thus lower temperatures may be preferred in instances where a maximum amount of oxidation is desired. Higher temperatures than 100° C. may be employed under superatmospheric pressure. Provided that the pressure is sufficient at the existing temperature to maintain liquid phase conditions, the temperature may be 100°–200° C. or higher but such extreme reaction conditions are not necessary and are usually avoided.

Inexpensive reaction vessels or open vats, with or without agitators and other simple auxiliary equipment, are satisfactory and may be used with good results. The period of treatment may be varied over wide ranges. It is only necessary that the aqueous medium be intimately contacted with the lignite for a period of time sufficient for the reaction to occur and continued treatment is not deleterious. The minimum period of treatment will vary to some extent with the remaining conditions, such as the particle size of the lignite, the concentration of the catalyst, the pH value of the aqueous medium and the reaction temperature. The period of treatment may vary, for example, from approximately 15 minutes or less to 24 hours or more but it is usually from about 1 to 3 hours. As a general rule, the amount of oxidation increases with time provided all of the remaining conditions of treatment remain the same. Lignite has active sites or carbon atoms such as carbon-to-carbon double or triple bonds, carbon-to-oxygen bonds, carbon-to-sulfur bonds, carbon-to-nitrogen bonds, carbon-to-metal bonds, carbon attached to an electro-negative group, and carbon bonded or otherwise attached or attracted to a dissimilar substrate which is a component of the lignite. The catalyst of the present invention causes the liquid water in the aqueous treating medium to exhibit very unusual and heretofore unrecognized properties in the presence of lignite having the aforementioned active carbon atoms or active sites. While the exact nature of the reaction is not known at the present time, it appears that water or some component of water reacts with or alters the active carbon atoms or active sites to thereby produce pronounced chemical and/or physical changes. For example, the lignite may be oxidized to produce carboxylic acids and especially humic acids. It is also possible to fix nitrogen in the presence of an atmosphere containing elemental nitrogen. Additionally, combustable sulfur, nitrogen, and deleterious substances in general are altered to permit their removal by prior art techniques such as by extraction in the aqueous treating medium or with solvents subsequent to the treatment. Additionally, metal values present in the lignite are rendered soluble or solubilized. The treated particles have a much higher water content than before treatment. Following treatment, the aqueous treating medium contains the water soluble constituents of the treated lignite.

When the aqueous medium containing the catalyst is contacted with the lignite there is a period of activation during which there is little or no reaction. This activation period may be eliminated or reduced markedly by pre-treating a fresh catalyst suspension with a small portion of the lignite, or by using a recycled catalyst solution from a previous treatment. In a preferred variant, all or part of the aqueous catalyst suspension is recycled so that an activated catalyst is always available for contacting with fresh portions of the lignite. The activated aqueous catalyst suspension thus produced is much more effective.

In a further variant of the invention, the lignite is treated with an oxidizing agent before, during or following treatment with the aqueous medium containing the catalyst. The oxidizing agent may be air, elemental oxygen, ozone, peroxides such as hydrogen peroxide or the alkali metal peroxides, or other suitable oxidizing agents. The lignite is reacted with the oxidizing agent in an amount to partially oxidize or artificially weather it without combustion. For example, air or elemental oxygen may be bubbled through the aqueous medium while in contact with the lignite, or the lignite may be intimately contacted with air or elemental oxygen at elevated temperature prior to treatment with the aqueous medium. The oxidation of the lignite often may be enhanced by treating with the aqueous catalyst suspension at temperatures approaching the freezing point, such as about 0°–10° C. and preferably about 0°–4° C. The degree of oxidation is also often controlled to some extent by the materials used in constructing the reaction vessel and the materials of construction of auxiliary apparatus in contact therewith such as agitators. Surprisingly, constructing the equipment from nonconductors of electricity such as polyolefins results in a maximum degree of oxidation under a given set of operating conditions. Constructing the equipment from good conductors of electricity such as steel and other metals results in a minimum degree of oxidation for a given set of treating conditions, whereas constructing the equipment from glass or ceramic materials results in an intermediate degree of oxidation.

It is not necessary to separate the catalyst suspension from the treated lignite. For example, in many instances it is advantageous to evaporate the water content of the aqueous suspension, either at atmospheric pressure or preferably under reduced pressure, to thereby deposit the catalyst micelles on the treated lignite. When this is done, addition of water reactivates the catalyst micelles and the lignite may be subjected to a further treatment with the aqueous catalyst suspension until it is fully solubilized.

It is understood that the lignite is treated with an aqueous catalyst suspension until it is solubilized therein. The terms "solution", "solubilized," etc., as used herein when referring to this product are intended to embrace true solutions as well as aqueous media containing finely divided suspended substances which are not in true solution. It is also understood that the lignite solution, which contains the novel catalyst suspension described hereinbefore as an ingredient, may be substituted for the aqueous catalyst suspension per se in the method of the invention. It is only necessary to substitute a like amount of the catalyst-containing lignite solution for the aqueous catalyst suspension per se, based upon the dry solids weight of the catalyst present in each instance.

In practicing one presently preferred variant, the lignite is treated initially with the aqueous catalyst suspension following the aforementioned general procedure to produce a catalyst treated lignite product. This initial treatment may involve admixing the particulate lignite with the aqueous catalyst suspension and allowing it to soak at ambient temperature for a substantial period of time such as 1–24 hours and preferably for about 15 hours. While this initial soaking period is not essential, it appears to improve the uniformity of the results without producing adverse effects in instances where it is not needed. The initial pH value of the admixture is approximately 8–11, and during the soaking period, the pH value gradually drops to approximately 4–6.5 and preferably about 5–6. The admixture is then heated to an elevated temperature such as about 60°–100° C. and preferably about 90°–100° C. with stirring for approximately 0.5–5 hours and for best results approximately 1–3 hours. Thereafter a strong base such as sodium hydroxide is added in an amount to adjust the pH to the initial value of approximately 8–11 and preferably about 9–10, followed by continued heating with agitation until the pH value gradually drops again to approximately 4–6.5 and preferably about 5–6. In instances where the pH value remains above this latter range, then additional untreated lignite may be added in an amount to lower the pH level. The water is evaporated from the admixture without filtering as valuable ingredients are dissolved in the aqueous treating medium. Conventional air drying at ambient or elevated temperature or vacuum drying is usually preferred. The dry catalyst treated lignite product has the catalyst micelles initially present in the aqueous treating medium deposited thereon and it may be stored for long periods of time while awaiting further treatment and use. The aqueous catalyst suspension used in the aforementioned initial treatment of the lignite is preferably concentrated and may be a catalyst suspension as produced by Examples I–IV appearing hereinafter.

The dry catalyst treated lignite thus prepared may be admixed with additional aqueous catalyst suspension, which also is preferably concentrated and may be as produced by Examples I–IV, in an amount to prepare an oily paste-like admixture. Approximately equal parts by weight of the catalyst treated lignite and aqueous catalyst suspension usually produce good results. This paste-like admixture may be easily dissolved in water and/or diluted catalyst suspension in amounts to produce a solution containing the desired amounts of dissolved lignite and/or catalyst on a dry solids basis for use in a given environment. It is only necessary that the catalyst be present in the catalytic amounts as described hereinbefore in the section on catalyst preparation, and the concentration of dissolved lignite may be as described below.

The concentrations of the catalyst suspension and the dissolved lignite solids in the solution may vary over extremely wide ranges. In a number of instances, the concentrations thereof are determined to some extent by the specific end use of the solution. Also, it is often advantageous to provide a concentrated solution which is diluted at the time of use. As a general rule, the concentration of catalyst solids in the solution is within the ranges aforementioned in the section on the preparation of the catalyst. The concentration of dissolved lignite in the solution may vary from about 0.01 to 0.1 part per million up to about 10% to 20% by weight. Solutions containing at least 500 parts per million, and preferably at least 600–700 parts per million, of dissolved lignite exhibit pronounced bacteriostatic and/or fungistatic properties and are often preferred for this reason. Solutions for general use usually contain about 0.5–500 parts per million, and preferably about 100–200 parts per million, of dissolved lignite and catalyst solids within the preferred ranges aforementioned, although more concentrated solutions may be provided initially for dilution. As a general rule, the solutions usually contain about 1–2% by weight or less of dissolved lignite.

Some naturally occurring lignites may contain metal values or other substances which are undesirable when the lignite solutions are used for certain purposes. In a further variant of the invention, such undesirable substances are removed from the lignite and/or rendered soluble in an extraction solvent in a pretreatment step with the catalyst suspension. For example, the lignite may be treated with an aqueous suspension of the catalyst following the usual practice until the undesirable substances are solubilized in the aqueous medium or rendered soluble in an extraction solvent. The period of treatment to accomplish this purpose may vary over wide ranges, such as from about 10 minutes to 10 hours or longer, or until the particles of lignite take on a weathered appearance similar to Leonardite and yet remain insoluble in the aqueous catalyst suspension and the extraction solvent. The treated lignite is separated from the catalyst suspension to thereby remove water soluble undesired substances. If water insoluble undesired substances are present, they may be removed by extraction with a suitable solvent. For example, aqueous mineral acids such as hydrochloric and sulfuric acid solutions may be used to remove acid soluble undesired constituents. Similarly, aqueous bases such as sodium, potassium and ammonium hydroxide may be used to remove undesired substances which are soluble in alkaline solutions. Additionally, liquid organic solvents such as liquid hydrocarbons, chlorinated hydrocarbons, alcohols, ketones and esters may be used to extract organic solvent soluble undesired substances. The resultant extracted lignite, which is now substantially free of undesired substances, is then further treated with the aqueous catalyst suspension until it is solubilized and a solution thereof may be prepared as previously discussed.

The concentrations of the catalyst and the solubilized lignite in the lignite solution are calculated by weight and on a dry solids basis. The lignite solids should be thoroughly air dried before weighing.

The invention is further illustrated by the following specific examples, which are for purposes of illustration only and are not limiting to the spirit or scope of the appended claims.

EXAMPLE I

This example illustrates one presently preferred process for preparing the novel catalyst used in practicing the invention.

Anhydrous calcium chloride in an amount of 0.66 gram and magnesium sulfate heptahydrate in an amount of 1.32 grams were dissolved in two liters of deionized water with stirring and warming until solution was complete. Then 95 grams of sodium silicate pentahydrate having a molecular ratio of sodium oxide to silicon dioxide of 1:1 were added to the solution with stirring and continued warming to produce a white colloidal suspension of the reaction product.

After setting for 10 minutes, the colloidal suspension was heated to 80° C. and sulfated castor oil in an amount of 201 grams was added with stirring. The average molecular weight of the sulfated castor oil was 940 and it contained 50% of water. The turbidity lessened somewhat as the colloidal suspension was heated at 80°–90° C. for one hour with vigorous stirring to produce catalyst micelles. The aqueous suspension of catalyst micelles thus prepared had a viscosity similar to that of water and it was used as a catalyst as noted hereinafter.

A dry or solid catalyst concentrate was prepared in a further run by evaporating water from the initially prepared aqueous catalyst suspension. The resulting dry catalyst concentrate was resuspended in water and there was no substantial loss of catalytic activity. In still other runs, the catalytic activity of the aqueous suspension of catalyst as initially prepared, the diluted aqueous suspension of catalyst, and the reconstituted aqueous catalyst suspension was enhanced by freezing and thawing.

EXAMPLE II

This example illustrates the preparation of additional catalyst suspensions.

Five suspensions of the catalyst were prepared from the same ingredients as used in Example I and following the general procedure of Example I. The ratios of ingredients were varied as follows:

| Ingredient | Amount of Ingredient | | | | |
|---|---|---|---|---|---|
| | Run 1 | Run 2 | Run 3 | Run 4 | Run 5 |
| Deionized water | 2 l | 1.5 l | 1.5 l | 1.5 l | 0.25 l |
| $CaCl_2$ | 0.66 g | 0.5 g | 0.5 g | 1.0 g | 0.5 g |
| $MgSO_4 \cdot 7H_2O$ | 1.32 g | 1.0 g | 1.0 g | 2.0 g | 1.0 g |
| $Na_2SiO_3 \cdot 5H_4O$ | 165 g | 132 g | 71 g | 185 g | 71 g |
| Sulfated Castor oil (approximately 50% by weight $H_2O$) | 100 ml | 150 ml | 150 ml | 200 ml | 150 ml |

The catalyst suspensions prepared by the above five runs were used as noted hereinafter.

EXAMPLE III

This Example illustrates a further presently preferred process for preparing the catalyst of the invention.

Anhydrous calcium chloride in an amount of 0.66 gram and magnesium sulfate heptahydrate in an amount of 1.32 grams were dissolved in one liter of soft water heated to 80° C. Then 95 grams of sodium silicate pentahydrate was added to the resulting solution with stirring to produce a suspension of finely divided particles of the reaction product. The sodium silicate pentahydrate contained approximately 0.12 gram of aluminum when calculated as $Al_2O_3$ and a somewhat smaller amount of zinc when calculated as ZnO.

The suspension of the reaction product was maintained at 80° C. and stirred for one-half hour. Then an aqueous solution prepared by admixing 75 grams of sulfated castor oil with 100 milliliters of water was added slowly with stirring. The stirring was continued for one-half hour thereafter while maintaining the reaction mixture at 80° C. to produce catalyst-containing micelles.

The sulfated castor oil contained 6.5–7% of organically combined $SO_3$ on a dry basis, 0.9–1.1% of combined alkali when calculated as sodium oxide, no free alkali, and 50% ± 1% of material volatile at 105° C., which was mostly water. The average molecular weight of the sulfated castor oil molecule was approximately 400 grams per mole.

The above prepared suspension of catalyst was placed in plastic containers awaiting testing and use. The catalyst suspension was tested and was rated as a superior catalyst. It was possible to add from 1,000 to 10,000 parts of water to a portion of the catalyst suspension and sill obtain excellent catalytic activity. A further portion of the catalyst suspension was frozen and thawed, and then tested. The cooling and warming steps enhanced the catalytic activity.

EXAMPLE IV

The general procedure of Example III was followed with the exception of using 0.33 gram of anhydrous calcium chloride rather than 0.66 gram, 0.66 gram of magnesium sulfate heptahydrate rather than 1.32 grams, and 45 grams of sodium silicate pentahydrate rather than 95 grams. The remaining ingredients and steps in the Example III procedure for preparing the catalyst were not changed.

The resulting catalyst suspension was approximately one-half as concentrated as that prepared in Example III. Upon testing, it was found to be as effective as the catalyst of Example III when calculated on a dry solid basis. Cooling the catalyst suspension to temperatures approaching the freezing point or freezing, following by warming or thawing, also had a beneficial effect upon the catalytic activity.

EXAMPLE V

This Example illustrates the preparation of solutions from lignite which are useful in practicing the method of the invention.

Lignite from the Havelock Mine, New England, North Dakota was ground to minus 60 mesh (Tyler Screen) and 200 grams thereof was admixed with 250 ml of a catalyst suspension prepared in accordance with Example I and diluted with 1000 volumes of water. The admixture was treated for 2 hours at room temperature (72° F.) in a 1 quart Abbe Ball Mill using ⅜ inch ceramic balls. Following the treatment, the reaction mixture was filtered to obtain a glassy black pitch-like solid residue of treated lignite particles and a yellow liquid treating solution having a pH of 6.7.

The treated lignite particles were extracted with acetone to produce a dark red solution and a residue of acetone extracted particles. The acetone extracted particles were further extracted with 3 M hydrochloric acid to obtain a yellow-orange acidic extract solution and an acid extracted residue.

The acid extracted char was further treated with 1 M sodium hydroxide solution and the mixture set to a jet-black pitchlike substance. The solution was filtered with difficulty to yield a black thick liquid and a sodium hydroxide treated residue. When the residue was washed with water, the solid material peptized and passed through the filter. Thus, substantially all of the lignite was solubilized.

EXAMPLE VI

This Example illustrates the preparation of an aqueous solution of catalyst treated lignite.

Weathered lignite having a particle size of minus 80 mesh (Tyler Screen) was admixed in an amount of 50 pounds with 2.50 ml of the catalyst suspension prepared in accordance with Example I and 8 gallons of hot soft water having a temperature of 150° F. The admixture was heated and stirred and after five minutes, the pH value was approximately 5. The admixture was allowed to set without heating for 12 hours and then 2 pounds of flake caustic (78% sodium hydroxide) was added. The admixture was stirred for approximately 5 minutes and the pH was 5-6. The wet catalyst treated lignite was air dried and stored in a plastic container.

The above prepared catalyst treated lignite was admixed in an amount of 298 grams with 307 grams of the catalyst suspension prepared in accordance with Example I. The resultant moist solid was stored in an airtight container while awaiting the preparation of a solution. Thereafter, 5 grams of this admixture was added to one gallon of soft water. Substantially all of the treated lignite dissolved forming a dark opague blue-black solution. The solution contained the catalyst in a concentration equivalent to diluting the catalyst suspension of Example I with 1000 volumes of water and it also contained 700 parts per million of the dissolved catalyst treated lignite. The pH value was 7.

EXAMPLE VII

This Example illustrates the treatment of lignite from Havelock Mine, New England, North Dakota having a particle size such that 85% passed through a minus 85 mesh Tyler Screen.

An admixture of 70 pounds of the lignite, 300 ml of the catalyst suspension prepared in accordance with Example I and 8 gallons of soft water having a temperature of 150° F. was prepared. After 5 minutes of heating and stirring, the pH was 5 and 2.2 pounds of flake caustic soda (78% sodium hydroxide) was added. The pH of the resultant solution was 12 and after one-half hour of heating the pH was 11. The admixture was allowed to set for 12 hours.

Thereafter ½ of the treated lignite was air dried. A white encrustation appeared on the surface after drying. A second ½ portion of the treated lignite was kept moist with water for 2 days to determine if air oxidation continues provided the treated lignite is kept moist and basic. Upon testing, it was found that the air oxidation did continue. A white encrustation formed on the surface of the treated lignite when dry. The remaining ⅓ portion of the treated lignite was admixed with 2 gallons of hot soft water and thereafter 100 grams of sodium perborate was added. The temperature was 76° C. Thereafter, the treated lignite was air dried in the sun and no white encrustation developed on the surface. Lignite solutions are prepared from each of the above dry catalyst treated lignite products following the general procedure set out in the last paragraph of Example VI.

EXAMPLE VIII

This Example illustrates a further presently preferred process for preparing aqueous solutions of lignite which are useful in practicing the method of the invention.

Fifty pounds of North Dakota lignite was ground to minus 80 Tyler Mesh and admixed with five gallons of softened water containing 100 ml of the concentrated aqueous catalyst suspension as produced by Example I. The admixture was allowed to soak without heating for 15 hours. At the end of the soaking period, the pH value was 5 and the admixture was heated at 90°-100° C. with stirring for 3 hours. Sufficient flake sodium hydroxide was added to adjust the pH value to 11 and the heating and stirring was continued until the pH value had decreased to 5.

The water was removed from the resultant aqueous admixture of catalyst treated lignite by air drying. The dry catalyst treated lignite product thus prepared was stored in containers while awaiting the preparation of lignite solutions.

Approximately equal parts by weight of the catalyst treated air dried lignite and of the concentrated catalyst suspension prepared by Example I were admixed to produce a solid material having a paste-like consistency. Aqueous solutions of catalyst treated lignite were prepared from the paste having the following formulations:

TABLE I

| Formulation No. | 1 | 2 | 3 | 4 |
|---|---|---|---|---|
| Ingredient | | | | |
| Catalyst Treated Lignite paste, grams | 7.32 | 2.9 | 300 | 300 |
| Concentrated Catalyst Suspension prepared by Example I, liters | None | 2.4 | 1.0 | 2.0 |
| Soft water, liters | 3.875 | 16.0 | 17.4 | 16.4 |

Certain of the above formulations were used in examples as noted hereinafter.

Additional solutions of catalyst treated lignite are prepared in further runs by following the general procedure of this Example with the exception of substituting the catalyst suspensions prepared in accordance with Examples II, III and IV for the catalyst suspension of Example I. All of the catalyst suspensions are active and are useful in solubilizing the lignite. Comparable results are obtained when the amount of the catalyst to be used is based upon dry catalyst solids.

EXAMPLE IX

This Example illustrates the use of the aqueous catalyst suspension prepared by Example I in treating soil in accordance with the invention to improve the fertility thereof.

A plot of soil suitable for use in growing garden vegetables and field crops is divided into a first portion and a second portion. The first portion and the second portion are of substantially the same size and each portion is substantially equal in fertility initially. The first and second portions of the plot are plowed to loosen and pulverize the soil to a depth of approximately 4–6 inches.

The loose pulverized soil in the first portion of the plot is watered with a diluted catalyst suspension prepared by diluting the concentrated aqueous catalyst suspension as prepared by Example I with 1,000 volumes of water, and then adding one liquid ounce thereof to each gallon of the water. The second portion of the plot is watered with plain water. The first portion is watered by sprinkling the surface area with the diluted aqueous catalyst suspension in an amount equivalent to a layer 0.5 inch in depth. The second portion is watered by sprinkling the surface area with plain water in an amount equivalent to a layer 0.5 inch in depth. Thus, the first and second portions of the plot are watered with an equal volume of an aqueous medium. The diluted aqueous catalyst suspension applied to the first portion is allowed to percolate into the pulverized top soil layer, and then the top soil layer is reworked to uniformly admix the catalyst therein. Similarly, the plain water applied to the second portion is allowed sufficient time to percolate into the top soil, and the top soil layer is reworked to provide comparative conditions. Thereafter, rows are prepared in the first and second portions to form seedbeds for planting.

Equal lengths of rows in the first and second portions of the plot are planted with common garden vegetables, i.e., potatoes, string beans, lima beans, peas and beets using seed from the same source and under substantially identical conditions, and following the recommended spacing and depth of planting for each species of plant. Thereafter, the growing plants are cultivated under substantially identical conditions following the recommended practice for each species of plant. It will be apparent from the foregoing that the first and second portions of the plot, and the plants growing thereon, receive substantially identical treatment with the exception that the first portion is treated with the catalyst, and the second portion is not treated with the catalyst so as to provide comparative data.

The growing plants are observed periodically during the growing season and the observations are recorded for each of the two plots. Additionally, at the end of the growing season for each species of plant, the yields for each of the first and second portions of the plot are determined and recorded.

The plants in the first portion of the plot grow faster and are more vigorous and stronger, have a better color and general appearance, and are freer of disease than the plants grown in the second portion of the plot. The beneficial effects noted in the plants grown in the first portion continue throughout the normal lifespan of the plants. Additionally, the yields from the plants grown in the first portion are much higher than in the second portion. The plants grown in the first portion are also less affected by adverse weather, temperature and other environmental conditions. Thus, inasmuch as the first and second portions have received identical treatment with the exception of only the first portion being treated with the catalyst, it is apparent that the presence of a catalytically effective amount of the catalyst increases the fertility of the treated soil, and that it also provides the growing plants with an environment which results in greater resistance to disease and/or adverse environmental conditions.

EXAMPLE X

This Example illustrates the use of formulation No. 3 of Example VIII in treating soil in accordance with the invention to increase the fertility thereof.

The general procedure of this Example is the same as that of Example IX, with the exception of substituting a diluted formulation No. 3 prepared in accordance with Example VIII for the diluted catalyst suspension used in Example IX. Formulation No. 3 of Example VIII is diluted at the rate of one liquid ounce thereof per gallon of water, and the diluted solution of catalyst and lignite is used in treating the first portion of the plot in this Example.

The plants are observed periodically during the growing season as in Example IX, and the results are recorded. The plants growing in the first portion of the plot are stronger and grow more vigorously, have a better color and general appearance, and are freer of disease than the plants growing in the second portion of the plot. These beneficial effects continue throughout the lifespan of the plants. The yields from plants growing in the first portion are much higher than the yields from the plants grown in the second portion. Furthermore, these beneficial effects on the plants growing in the first portion of the plot in this Example are even more marked than those observed and reported for the first portion of the plot in Example IX. Thus, the catalyst treated lignite in combination with the catalyst per se produces even better results.

EXAMPLE XI

This Example illustrates the use of plant nutrients in combination with the catalyst and/or catalyst treated lignite of the invention in increasing the fertility of soil.

In a first series of runs, the general procedures of Examples IX and X are followed with the exception of, in each instance, also adding a soluble chemical fertilizer to the diluted catalyst and/or catalyst treated lignite solution used in treating the first portions of the plots, and to the plain water used in treating the second portions of the plots. A commercially available fertilizer identified as Peters 15–10–30 is used, and thus the fertilizer contains 15% of available nitrogen, 10% of available phosphorous, and 30% of available potassium. In the first series of runs, the fertilizer is added to the aqueous medium at a rate to provide 300 parts per million of nitrogen, which is usually the recommended amount.

In a second series of runs, the same procedure is followed as in the above described first series of runs, with the exception of using only one-half as much of the fertilizer. Thus, the diluted catalyst and/or catalyst treated lignite solution used in watering the first portions of the plots contains the fertilizer in an amount to provide only 150 parts per million of nitrogen, or only one-half of the recommended amount.

It was observed that the plants grown in the first portions of the plots under the conditions of the second series of runs were as vigorous, or even more vigorous under arid conditions, than those grown in the first portions of the plots under the conditions of the first series of runs. Thus, reducing the amount of chemical fertilizer to only one-half of that normally recommended gives as good or better results than using the recommended amount. The various beneficial effects noted previously in Examples IX and X in growing plants in the first portions of the plots were also noted in this Example. In addition thereto, the rate of growth and the yield were enhanced. Thus, the addition of a chemical fertilizer to the diluted catalyst and/or catalyst treated lignite solutions results in even more vigorous and faster growth and higher yields.

EXAMPLE XII

In a further series of runs, the general procedure of Example IX is repeated with the exception of using catalyst suspensions prepared by the procedures of Examples II–IV. Comparable results are obtained to those reported in Example IX on a dry catalyst solids basis.

In another series of runs, the test procedure of Example X is repeated with the exception of using catalyst suspensions on the same dry solids basis, but prepared by the procedures of Examples II–IV, for the preparation of lignite solutions in accordance with the procedures of Examples VI through VIII. The resulting lignite solutions are then substituted for Formulation No. 3 of Example VIII on a dry solids basis. Results comparable to those reported in Example X are obtained.

In a further series of runs, the test procedure of Example X is followed with the exception of substituting the lignite solutions identified as Formulations No. 1, 2 and 4 of Example VIII for Formulation No. 3 on a dry solids basis. Results comparable to those reported in Example X are obtained.

EXAMPLE XIII

This Example illustrates the preparation of potting soil treated with the catalyst and/or catalyst treated lignite of the invention, with or without plant nutrients, and the use thereof in growing household plants.

The general procedures of Examples IX, X and XI are repeated up through the steps of watering the first and second portions of the plots and allowing the aqueous media to percolate into the top soil layer. At that time, moist top soil is collected from each of the first and second portions of the plots and used in preparing treated soil which is especially useful in the growing of household plants, and plants in hothouses, greenhouses, and the like.

In the first series of runs, and moist soil from the various first and second portions of the plots is used directly as a potting soil for household plants including ivy, philodendron, geraniums and African Violets. The plants are grown at normal room temperature and using the recommended lighting and watering procedures for each species of plant. In each instance, the plants grown in soil which has been treated in accordance with the invention are stronger and more vigorous, freer of disease, and are capable of better withstanding adverse environmental conditions. The plants are also more beautiful and pleasing in appearance.

In a second series of runs, the moist top soil is first dehydrated by air drying and is then used in potting household plants. The results of this series of runs are comparable to those reported in the first series of runs.

In a third series of runs, the moist top soil is partially air dried to a slightly moist state, and then is packaged in plastic bags similar to those commonly used to package potting soil for sale in gardening outlets. The packaged top soil is stored for several months, and then is used in potting household plants. The results of this run are comparable to those reported above in the first series of runs. Thus, the treated soil may be stored for long periods of time without noticable deterioration.

I claim:

1. A method of improving the fertility of soil comprising intimately contacting the soil with water containing a catalytically effective amount of a catalyst, the said catalyst being prepared by a process comprising
   admixing a water soluble alkali metal silicate with an aqueous medium containing a dissolved substance which is a source of calcium ion and a dissolved substance which is a source of magnesium ion,
   the aqueous medium containing said dissolved substances in amounts to provide between about $1 \times 10^{-4}$ and $1 \times 10^{-1}$ mole per liter each of calcium ion and magnesium ion,
   the aqueous medium containing said dissolved substances in amounts to provide a molar ratio of calcium ion to magnesium ion between about 2.0:1.0 and 1.0:2.0,
   the alkali metal silicate having an alkali metal oxide to silicon dioxide ratio between about 0.9:1.0 and less than 2.0:1.0 and being admixed with the aqueous medium in an amount of about 0.05–2 moles per liter,
   reacting the alkali metal silicate with said dissolved substances providing calcium ion and magnesium ion to produce an aqueous suspension of finely divided particles of the reaction product,
   admixing a micelle-forming surfactant with the aqueous medium in an amount to form catalyst micelles comprising said finely divided particles upon agitating the aqueous medium, and
   agitating the aqueous medium containing the finely divided particles and surfactant to form said catalyst micelles.

2. The soil characterized by improved fertility prepared by the method of claim 1.

3. The method of claim 1 wherein in the process for preparing the catalyst, said ratio of calcium ion to magnesium ion is between about 1.5:1.0 and 1.0:1.5.

4. The method of claim 1 wherein in the process for preparing the catalyst, said ratio of calcium ion to magnesium ion is about 1.0:1.0.

5. The method of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

6. The method of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter of calcium ion and magnesium ion.

7. The method of claim 1 wherein in the process for preparing the catalyst, about 0.2–0.3 mole per liter of the alkali metal silicate is admixed with the aqueous medium.

8. The method of claim 1 wherein in the process for preparing the catalyst, the alkali metal silicate has an alkali metal oxide to silicon dioxide ratio between about 0.9:1.0 and 1.2:1.0.

9. The method of claim 1 wherein in the process for preparing the catalyst, the alkali metal silicate has an alkali metal oxide to silicon dioxide ratio of about 1.0:1.0.

10. The method of claim 1 wherein in the process for preparing the catalyst, about 0.001–0.1 mole per liter of the surfactant is admixed with the aqueous medium.

11. The method of claim 1 wherein in the process for preparing the catalyst, the surfactant comprises sulfated castor oil.

12. The method of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.1-1 mole per liter of the alkali metal silicate is admixed with the aqueous medium, and the alkali metal silicate has an alkali metal oxide to silicon dioxide ratio between about 0.9:1.0 and 1.2:1.0.

13. The method of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2-0.3 mole per liter of the alkali metal silicate is admixed with the aqueous medium, and the alkali metal silicate has an alkali metal oxide to silicon dioxide ratio of about 1.0:1.0.

14. The method of claim 13 wherein in the process for preparing the catalyst, the alkali metal metasilicate is sodium metasilicate having an alkali metal oxide to silicon dioxide ratio of about 1.0:1.0.

15. The method of claim 13 wherein in the process for preparing the catalyst about 0.03-0.07 mole per liter of the surfactant is admixed with the aqueous medium.

16. The method of claim 15 wherein in the process for preparing the catalyst, the sufactant comprises sulfated castor oil.

17. The method of claim 16 wherein in the process for preparing the catalyst, the alkali metal metasilicate is sodium metasilicate having a sodium oxide to silicon dioxide ratio of about 1.0:1.0.

18. The method of claim 17 wherein in the process for preparing the catalyst, at least 25% of the hydroxy groups of the castor oil are sulfated, and about 0.03-0.07 mole per liter of the sulfated castor oil is admixed with the aqueous medium.

19. The method of claim 13 wherein in the process for preparing the catalyst, the alkali metal silicate is sodium metasilicate and it is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

20. The method of claim 1 wherein the said water intimately contacted with the soil also contains catalyst treated lignite, the lignite being pretreated with an aqueous medium containing the said catalyst defined in claim 1 until it is soluble in the said water.

21. The soil characterized by improved fertility prepared by the method of claim 20.

22. The method of claim 20 wherein in the process for preparing the catalyst, the alkali metal silicate is admixed with an aqueous medium containing said dissolved substances in amounts to provide between about $1 \times 10^{31\ 3}$ and $6 \times 10^{-3}$ mole per liter each of calcium ion and magnesium ion, the ratio of calcium ion to magnesium ion is between about 1.5:1.0 and 1.0:1.5, about 0.1-1 mole per liter of the alkali metal silicate is admixed with the aqueous medium, and the alkali metal silicate has an alkali metal oxide to silicon dioxide ratio batween about 0.9:1.0 and 1.2:1.0.

23. The method of claim 20 wherein in the process for preparing the catalyst, the alkali metal silicate is sodium metasilicate and it is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2-0.3 mole per liter of the sodium metasilicate is admixed with the aqueous medium, and the sodium metasilicate has a sodium oxide to silicon dioxide ratio of about 1.0:1.0.

24. The method of claim 20 wherein in the process for preparing the catalyst, the alkali metal silicate is sodium metasilicate and it is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

* * * * *